United States Patent [19]

Nicolas et al.

[11] Patent Number: 4,762,132
[45] Date of Patent: Aug. 9, 1988

[54] DEVICE FOR SCANNING OBJECTS BY MEANS OF ULTRASOUND ECHOGRAPHY

[75] Inventors: Jean-Marie Nicolas; Jean-Luc Bernatets, both of Paris, France

[73] Assignee: U.S. Philips Corporation, New York, N.Y.

[21] Appl. No.: 851,837

[22] Filed: Apr. 14, 1986

[30] Foreign Application Priority Data

Apr. 19, 1985 [FR] France ................... 85 05952

[51] Int. Cl.$^4$ ........................................... A61B 10/00
[52] U.S. Cl. .................................................. 128/660
[58] Field of Search ............... 128/660, 661, 662, 663; 73/602, 614, 629, 633

[56] References Cited

U.S. PATENT DOCUMENTS 4,452,082  6/1984  Miwa ..................................... 73/602
4,545,250  10/1985  Miwa ..................................... 73/602

OTHER PUBLICATIONS

The Fourier Transform and Its Applications, by Ron Bracewell, McGraw-Hill Book Company, 1965, pp. 7-11, 219-221, 254-257.
"Tissue Ultrasonic Attenuation Well Modelized by a Mellin Convolution", by M. Auphan and J. M. Nicolas, published in Acoustical Imaging, vol. 12, Plenum Publishing Corp., 1982.

Primary Examiner—William E. Kamm
Assistant Examiner—George Manuel
Attorney, Agent, or Firm—Jack E. Haken

[57] ABSTRACT

A device for scanning objects, notably biological tissues, by means of ultrasound echography, which device includes at least one ultrasound transducer (10) which is connected to a transmitter stage (20) for the repeated transmission of ultrasound waves to the object to be examined, and to a receiver stage for receiving the echoes reflected in the direction of the transducer. The device in accordance with the invention is characterized mainly in that the receiver stage includes:
(A) a transformation device (110) for transforming the echographic signal by calculation of the Mellin transform of this signal;
(B) an arithmetic device (120) for calculating a correction function by transformation of the attenuation function;
(C) a processing device (130) which consists of a series connection of a multiplier circuit (131) for multiplying the respective output signals of the transformation devices (110) and (120) and a circuit (132) for calculating the inverse Mellin transform of the signal thus obtained.
(D) a processing device (140) for processing the output signal of the arithmetic circuit (132) for calculating the inverse Mellin transform for the display of images of the region scanned and/or data which are representative of the region scanned.

7 Claims, 4 Drawing Sheets

DEVICE FOR SCANNING OBJECTS BY MEANS OF ULTRASOUND ECHOGRAPHY

The invention relates to a device for scanning objects, notably biological tissues, by means of ultrasound echography, which device includes at least one ultrasound transducer which is connected to a transmitter stage for the repeated transmission of ultrasound waves to the object to be examined, and to a receiver stage for receiving the echoes which are reflected in the direction of the transducer by the obstacles encountered by these waves in the object.

U.S. Pat. No. 4,016,750 describes an ultrasound echography apparatus which in known manner includes a transducer which is connected to a transmitter stage for the transmission of ultrasound waves, and to a receiver stage for receiving echoes which includes a display circuit for the display of images which are representative of regions of the object scanned. Between the transducer and said circuit there are a number of intermediate circuits, including a circuit which is composed of a variable-gain amplifier and a controllable filter. This amplifier and this filter correct the gain and the filter characteristics, respectively, as a function of the distance travelled by the ultrasound waves through the tissues scanned.

It is an object of the invention to provide an ultrasound echography apparatus which also corrects for the decreasing of the intensity of the ultrasound signal and the selective attenuation of the high frequencies as a function of the distance travelled, its construction and operation, however, being completely different from the construction and operation disclosed in said Patent Specification.

To achieve this, the device in accordance with the invention is characterized in that the receiver stage includes:

(A) a transformation device for transforming the echographic signal by calculation of the Mellin transform of this signal;

(B) an arithmetic device for calculating a correction function by transformation of the attenuation function, the inverse value being calculated of the Mellin transform of the attenuation function associated with an attentuation value corresponding to at least one region of the object to be scanned;

(C) a processing device which is composed of a series connection of:
  (1) a multiplier circuit for multiplying the respective output signals of the transformation devices specified sub (A) and (B);
  (2) an arithmetic circuit for calculating the inverse Mellin transform of the signal thus obtained;

(D) a processing device for processing the output signal of this arithmetic circuit for calculating the inverse Mellin transform for the display of images of the region scanned and/or data which are representative of the region scanned.

This construction is based onthe principle that an overall correction of both adverse effects of the attenuation is obtained by performing, in the receiver stage of the device, an approximation of the inverse mathematical transform of the integral transform which is referred to as a Mellin convolution (this integral transform is described in the article "Tissure ultrasonic attenuation well modelized by a Mellin convolution" by M. Auphan and J. M. Nicolas, published in Acoustical Imaging, Vol. 12, Plenum Publishing Corporation, 1982).

The invention will be described in detail hereinafter, by way of example, with reference to the drawings; therein:

Figure 1:
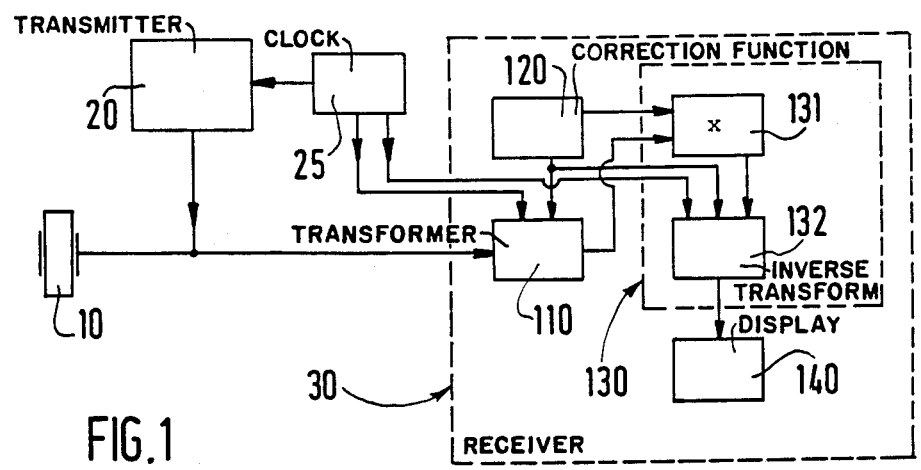
FIG. 1 shows an embodiment of the device in accordance with the invention.

The device shown in FIG. 1 includes an ultrasound transducer 10 which serves in the present embodiment for the transmission of ultrasound waves to the object to be examined by means of echography, as well as for the reception of the echoes reflected to the ultrasound transducer by the obstacles encountered by these waves in the region scanned. It will be apparent that for a satisfactory examination a coupling medium is arranged between the transducer and the region scanned; however, in order to simplify the drawing this region as well as the intermediate coupling medium have been omitted. It is to be noted that only one ultrasound transducer is used in this example; however, within the scope of the invention devices such as probes, linear arrays or other arrays of elementary transducers can be used for converting electric energy into ultrasound energy and vice versa.

The ultrasound waves transmitted by the transducer correspond to electric signals originating from a transmitter stage 20 which in known manner controls the repeated, generally periodic transmission of the waves in the direction of the object to be examined; the repetition frequency thereof is generally between 1 and 5 kHz and the frequency of the ultrasound waves is between 1 and 10 kHz, but these limits are by no means rigidly prescribed. The ultrasound echoes reflected by the various obstacles encountered by the ultrasound waves in the region scanned are received by the transudcer 10 in the receiving mode, the transducer then supplies electric signals correspond to these echoes to a receiver stage 30.

Between the transducer 10, the transmitter stage 20 and the receiver stage 30 there may be arranged an interface circuit (not shown), notably in order to prevent the receiver stage from being overdriven by the transmitter stage. The Figure also shows a clock circuit 25 which controls the successive operation of the stages.

The receiver stage 30 of the device in accordance with the invention includes a transformation device 110 for transforming the echographic signal in order to calculate the Mellin transform of this signal, an arithmetic device 120 for calculating a correction function by transformation of the attentuation function, said device calculating the inverse value of the Mellin transform of the attenuation function associated with a given attenuation value (described hereinafter) a processing circuit 130 for supplying an echographic signal which has been corrected in respect of the attenuation, and a display device 140 for treating the output signal of the device 130.

The processing device 130 itself includes a multiplier circuit 131 for multiplying the restrictive output signals of the transformation devices 110 and 120, and an arithmetic circuit 132 for calculating the inverse Mellin transform of the signal resulting from this multiplication.

The display device 140 of the present embodiment is formed by an image display device; however, depending on the intended application it could be also be any other device suitable for converting the output signals of the circuit 132 into qualitative or quantitave information. This is because according to the user's wishes images of the regions scanned can be displayed, or qualitative or quantitative data which are representative of the regions scanned can be supplied, or these various functions can be combined. In all cases, however, the scope of the invention is not restricted by the choice of the display device.

In the embodiment described thus far, the region scanned is formed by a slice of the object in which the attenuation value is substantially constant and assumed to be known in the form of a mean value, and the device 120 calculates the Mellin transform of this mean value with which the attenuation function is associated.

Figure 2:
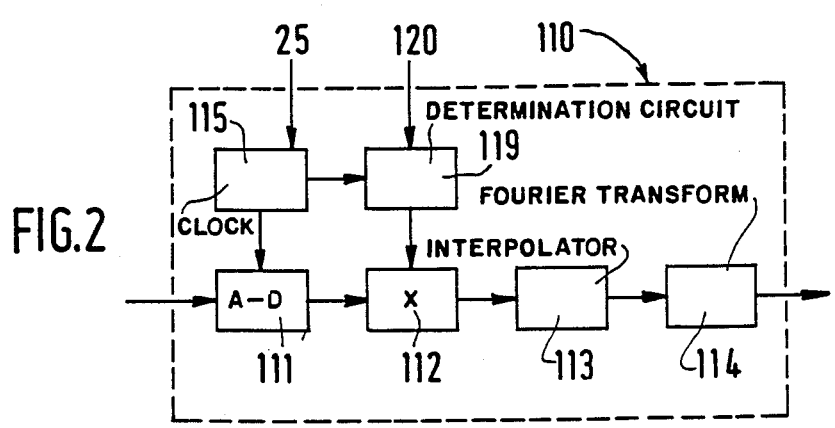
FIG. 2 shows a special embodiment of the transformation device for transforming the echographic signal, and the FIGS. 3 to 5 show alternative embodiments of this transformation device.

In a preferred embodiment as shown in FIG. 2, the transformation device 110 for transforming an echographic signal includes a series connection of an analog-to-digital converter 111, a multiplier circuit 112 for multiplying the signal thus digitized by a ramp voltage which increases linearly as a function of time, an interpolation circuit 113 for interpolation by linear-logarithmic conversion of the time scale, and an arithmetic circuit 114 for calculating the Fourier transform of the signal resulting from the interpolation. The time origin of the ramp signal is determined by a determination circuit 119 for determining the time reference, taking into account the distance between the transducer and the region for which an image or a representation is desired, and for determining, if necessary, the attenuation value (values) of the object. When the mean value of the attenuation between the transducer and the zone to be displayed or represented is known, this time reference is actually formed by the transit time between the transducer and this zone, multiplied by this value and divided by the mean value of the attenuation in the actual region scanned. A connection between the device 120 and the device 110 serves to transfer the mean value of the attenuation between the transducer and the zone scanned. Two supplementary connections, i.e. between the device 120 and the circuit 132, and between the clock circuit 25 and the circuit 132, serve to apply this mean attenuation value and time reference $t_o$, respectively, to the circuit 132.

The clock circuit 115 of the converter 111 has a linear scale (the pulses supplied are separated by uniform intervals) and from this clock circuit the linear ramp signal is generated in this case. As has already been mentioned the clock circuit 25 serves to control the clock circuit 115 or the other clock circuits of the receiver stage as in the following embodiments.

Figure 3:
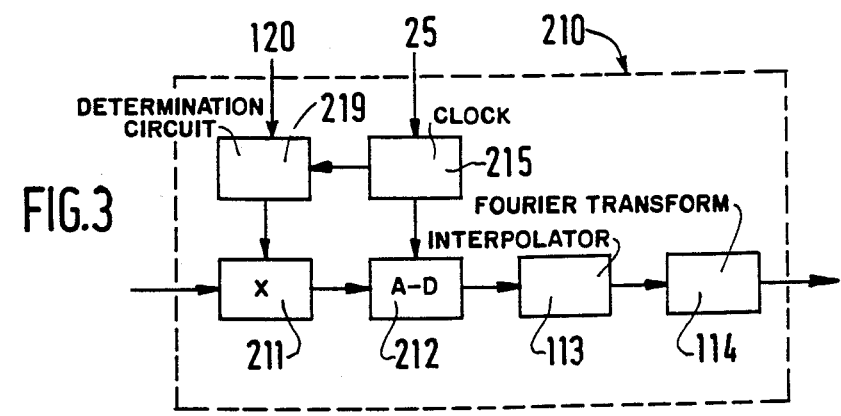

In a modified embodiment as shown in FIG. 3, the transformation device (now denoted by the reference numeral 210) for transforming the echographic signal operates according to the same principle as the device 110, and may include the following circuits: an analog multiplier circuit 211 for multiplying the echographic signal by a ramp signal, an analog-to-digital converter 212 whose clock circuit 215 also has a linear scale and applies the ramp signal to the multiplier circuit as before, and, as in the previous embodiment, the circuits 113 and 114. A determination circuit 219 for determining the time reference is connected to the clock circuit 215.

Figure 4:
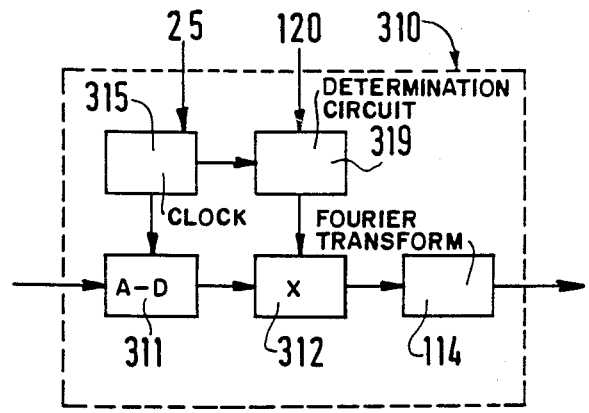
Figure 5:
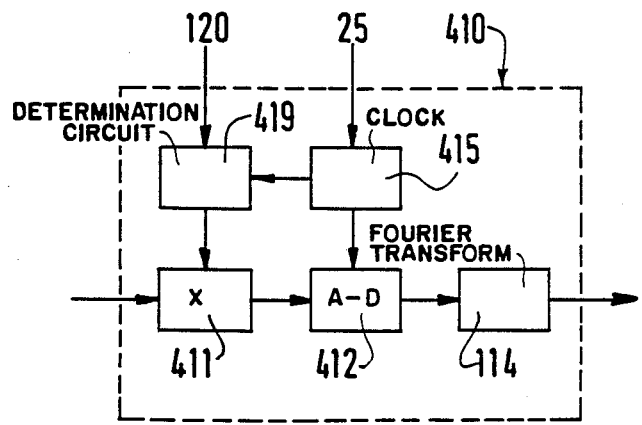

FIGS. 4 and 5 illustrate further alternative embodiments of the transformation device (310, 410) for transforming the echographic signal. The device 310 shown in FIG. 4 includes a series connection of an analog-to-digital converter 311 for the echographic signal, a multiplier circuit 312 for multiplying the digitized signal by a signal which is proportional to $\log(t-t_o)$, in which $t_o$ is the previously mentioned time reference, and the circuit 114. The device 410 shown in FIG. 5 includes a multiplier circuit 411 for multiplying the echographic signal, an analog-to-digital converter 412 for the signal thus obtained, and the circuit 114 again. In both cases the clock circuit (315 and 415, respectively) of the converter has a logarithmic scale. Like in the previous embodiment, a determination circuit 319, 419 for determining the time reference is connected to the clock circuits 315 and 415, respectively.

Figure 6:
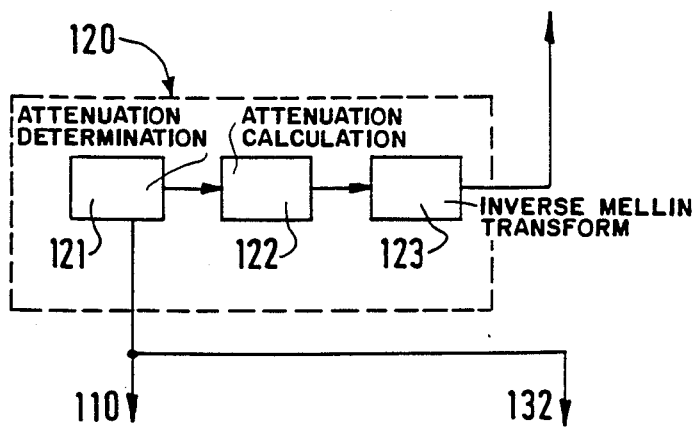
FIG. 6 shows a special embodiment of the transformation device for transforming the attenuation function.

The attenuation function transformation device 120 associated with said devices 110, 210, 310 or 410 can also be constructed in various ways, notably shown in FIG. 6. This transformation device then includes a series connection of a circuit 121 for predetermining an attenuation value which corresponds to a region of the object to be scanned (for example, by simply displaying on a display screen the means value previously assumed to be known and for predetermining an attenuation value corresponding to the zone between the transducer and the object scanned (for example, again by display on a display screen). The latter mean attenuation value is applied to the circuit 110 as well as to the circuit 132 (or to the alternative versions of these circuits). The device 120 furthermore includes an arithmetic circuit 122 for calculating the attenuation function associated with this value and an arithmetic circuit 123 for calculating the inverse value of the Mellin transform of this function.

Figure 7:
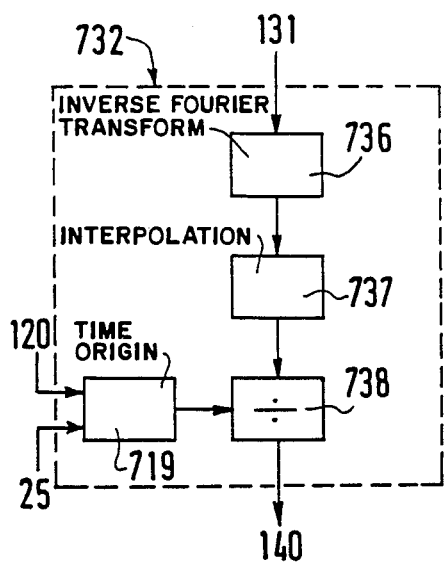
FIG. 7 shows a special embodiment of an arithmetic circuit which is included in the processing device and which serves to calculate the inverse Mellin transform.
Figure 9:
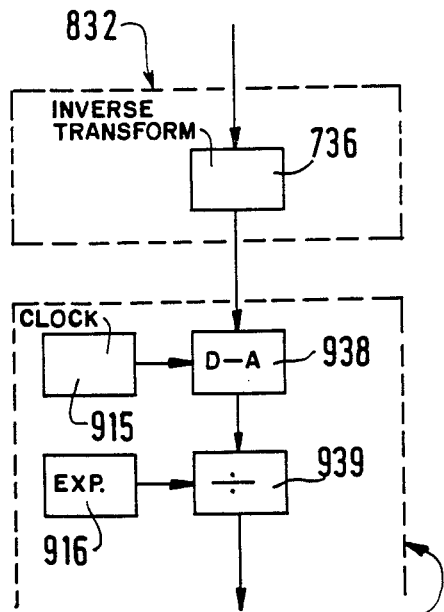
FIGS. 8 and 9 show two alternative embodiments of this processing device.
Figure 8:
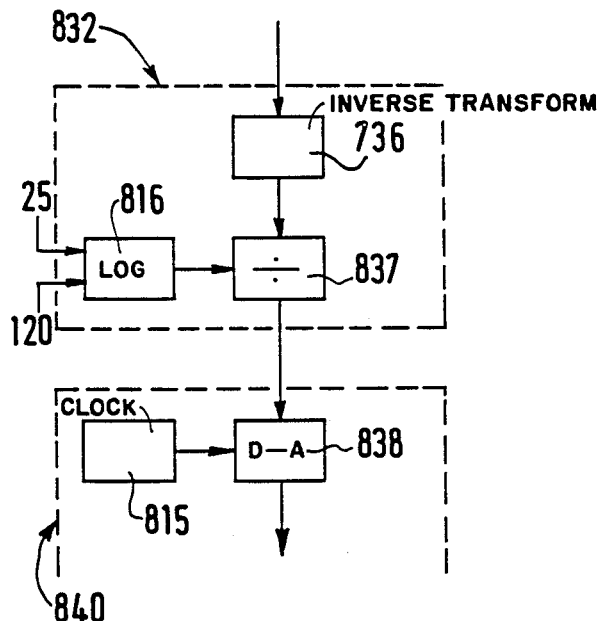

In the processing device which is associated, for example with one of the previously described transformation devices for the transformation of the echographic signal and with the transformation device described above for transforming the attenuation function, the arithmetic circuit for calculating the inverse Mellin transform may be constructed as follows. The arithmetic circuit is denoted by the reference numeral 732 (see FIG. 7) and includes a circuit 736 for calculating the inverse Fourier transform of the output signal of the multiplier circuit 131, an interpolation circuit 737 for interpolation by logarithmic-linear conversion of the time scale, and a divider circuit 738 for dividing the signal thus obtained by a ramp signal which increases in proportion to the time and whose time origin is determined (as before) by means of a determination circuit 719 for determining the time origin, which determination circuit is identical to the circuit 119. In a first alternative embodiment which is shown in FIG. 8, the circuits 737 and 738 may be replaced by a divider circuit 837 for dividing the signal originating from the circuit 736 by a signal which is proportional to $\log(t-t_o)$ and which is generated by a circuit 816. The display device 840 then includes a digital-to-analog converter 838 for the output signal of the divider circuit 837, the clock circuit 815 of this converter then having an exponential scale. In a second alternative embodiment as shown in FIG. 9, a digital-to-analog converter 938 is connected to the output of the circuit 736; this converter includes a clock circuit 915 having an exponential scale again and is followed by a divider circuit 939 for dividing the analog signal thus obtained by a signal which is proportional to $\exp(t-t_o)$ and which is generated by a circuit 916.

It will be apparent that the invention is by no means restricted to the foregoing embodiments and alternative versions thereof. Other alternatives are also feasible within the scope of the invention.

Figure 10:
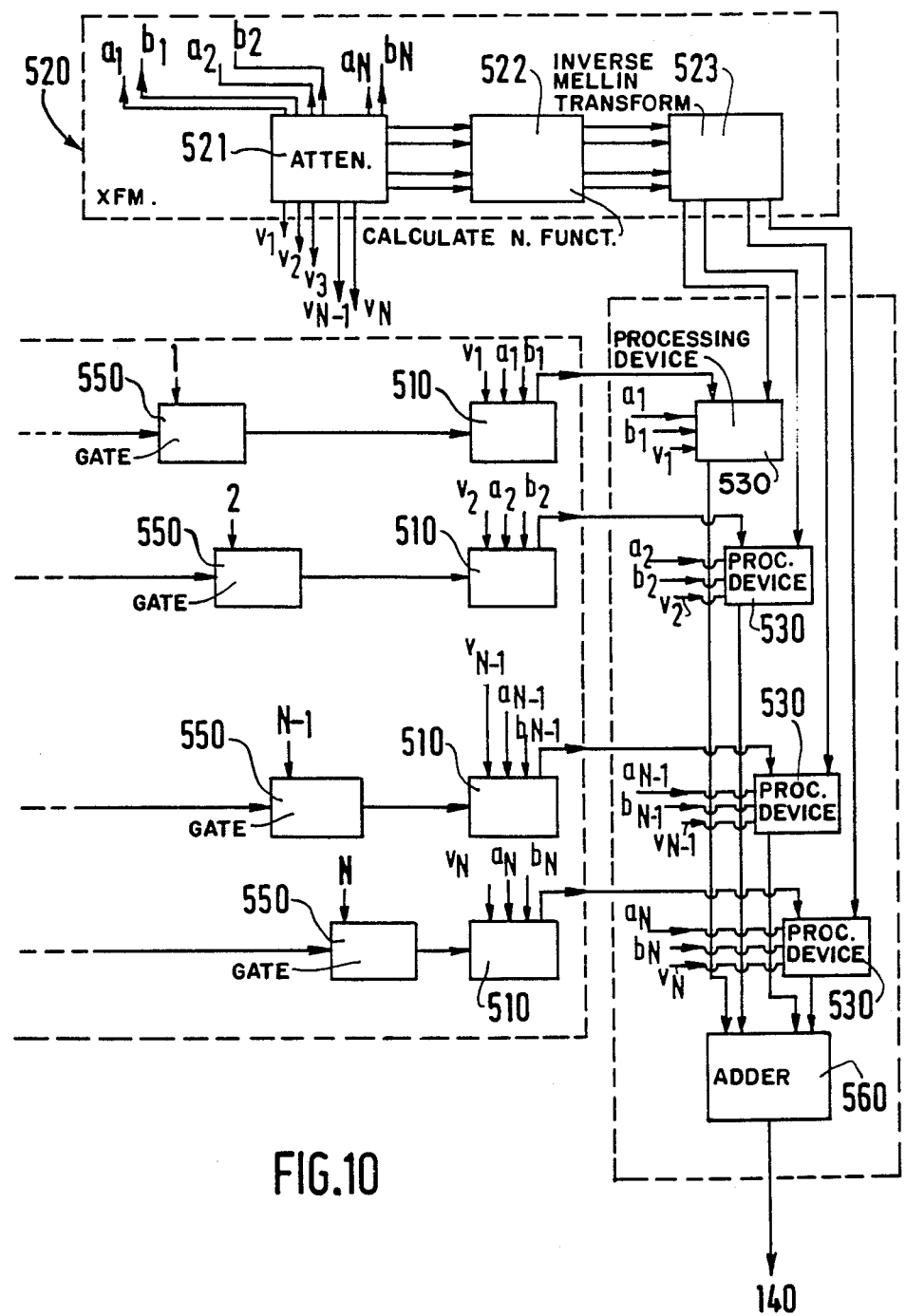
FIG. 10 shows an alternative embodiment of the transformation device for transforming the attentuation function and of the processing device.

FIG. 10 notably shows an alternative embodiment 520 of the transformation device for transforming the attenuation function, and also shows the processing device. The transformation device 520 for transforming the attenuation function includes a circuit 521 for predetermining a complete series of attenuation values $a_1, a_2, \ldots a_N$ which corresponds (in this case again at least on average) to successive regions of the object to be examined which are situated along the axis of propagation of the ultrasound waves, and for predetermining a series of values $b_1, b_2, \ldots b_N$ of the mean attenuation which coresponds to the respective zones situated between the transducer and the regions of the object to be examined. The circuit 521 may notably be one of the devices for scanning objects by means of ultrasound echography described by Applicant in previous Patent Applications, for example FR-A-2514910 and FR-A-2534707.

Thus, the circuit 521 supplies on the one hand an integer number of N attenuation values of the regions to be examined, and on the other hand N values of the mean attenuation corresponding to the mean value of the attenuation between the transducer and these regions to be examined, and finally N time values $v_1, v_2, \ldots v_N$ which denote the instants corresponding to the boundaries of said regions along the relevant axis of progagation. A circuit 522 calculates the N attenuation functions associated with the N attenuation values, and a circuit 523 calculates the inverse values of the Mellin transforms of these functions.

In the embodiment shown in FIG. 10, the device includes N gates 550 which are controlled by the N time values on the output of the circuit 521, each of said gates being controlled by one of these values. The N gates 550 are followed by N transformation devices 510 for transforming the echographic signals; these N channels (550, 510) are connected in parallel to the output of the transducer 10 when the transducer operates in the receiving mode (or to the output of the interface circuit if such a circuit is arranged between the transducer, the transmitter stage and the receiver stage). It is to be noted that the device includes N separate processing devices 530 which are followed by an adder circuit 560. Each device 510 receives a time value $v_1$ to $v_N$ and two attenuation values $a_1$ to $a_N$ and $b_1$ to $b_N$; the same holds good for each device 530. The output of the adder circuit 560 is connected to the input of the display device 140 which is also includes in the previously described embodiments.

What is claimed is:

1. In a device for scanning objects by means of ultrasound echography, which device includes at least one ultrasound transducer which is connected to transmitter means for the repeated transmission of ultrasound waves to an object to be examined, and to receiver means for receiving an echographic signal which represents echoes which are reflected to the transducer from the object, the improvement wherein the receiver means include:
   (A) transformation means (110) which calculate the Mellin transform of the echographic signal;
   (B) correction means (120) which calculate a correction function using an inverse value of the Mellin transform of an attenuation function which is associated with an attenuation value corresponding to at least one region of the object; and
   (C) a processing means comprising a series connection of:
      (1) first multiplier means (131) for multiplying the output signals of the transformation means and the first arithmetic means; and
      (2) inverse transformation means (132) which calculate the inverse Mellin transform of the output of the first multiplier means; and
   (D) display means (140) for processing the output signal of the inverse transformation means to display images of a region scanned and/or data which is representative of the region scanned.

2. A device as claimed in claim 1, wherein the transformation means includes a cascade connection of;
   (1) analog-to-digital converter means (111) connected to digitize the echographic signal, at linear scale sample intervals;
   (2) second multiplier means (112) which multiply the output of the analog-to-digital converter by a ramp signal which increases in proportion of the time;
   (3) interpolation means (113) which interpolate the output of the second multiplier means by linear-logarithmic conversion of the time scale; and
   (4) Fourier transform means (114) which calculate the Fourier transform of the output signal of the interpolation means.

3. A device as claimed in claim 1, wherein the transformation means include a cascade connection of:
   (1) second multiplier means (211) which multiply the echographic signal by a ramp signal which increases in proportion to time;
   (2) analog-to-digital converter means (212) which convert the output of the second multiplier means at linear scale sample intervals;
   (3) interpolation means (113) which interpolate the output of the analog-to-digital converter means by linear-logarithmic conversion of the time scale; and
   (4) Fourier transform means (114) which calculate the Fourier transform of the output of the interpolation means.

4. A device as claimed in claim 1, wherein the transformation means include a cascade connection:
   (1) analog-to-digital converter means (311) connected to digitize the echographic signal, at logarithmic scale sample intervals;
   (2) second multiplier means (312) which multiply the output of the analog-to-digital converter by a signal which is proportional to $\log(t-t_o)$, $t_o$ being a time reference which corresponds to a zone situated between the transducer and the zone for which an image or a representation is desired as well as to the attenuation in said separating zone; and (3) Fourier transform means (114) which calculate the Fourier transform of the output signal of the second multiplier means.

5. A device as claimed in claim 1, wherein the transformation means include a cascade connection of:
   (1) second multiplier means (411) which multiply the echographic signal by a ramp signal which increases in proportion to time;
   (2) analog-to-digital converter means (412) which convert the output of the second multiplier means at logarithmic scale sample intervals; and
   (3) Fourier transform means (114) which calculate the Fourier transform of the output of the analog-to-digital converter means.

6. A device as claimed in claim 4 or 5, wherein the correction means includes a cascade connection of:
   (1) circuit means (121) which predetermine an attenuation value which corresponds at least an average attenuation value in a region of the object to be scanned;
   (2) third arithmetic means (122) which calculate an attenuation function associated with said attenuation value; and
   (3) fourth arithmetic means (123) which calculate the inverse Mellin transform of said attenuation function.

7. A device as claimed in claim 6, characterized in that the fourth arithmetic means include:
   (1) fifth arithmetic means (736) which calculate the inverse Fourier transform of said attenuation function; and
   (2) divider means (837) which divide the output of the fifth arithmetic means by a signal which is proportional to $\log(t-t_o)$, $t_o$ being a time reference which corresponds to a zone situated between the transducer and the zone for which an image or a representation is desired as well as to the attenuation in said separating zone; and
   wherein the display device includes digital-to-analog converter means (838) which act on the output signal of the divider means, the clock circuit of said converter having at exponential scale sample intervals.

* * * * *